(12) United States Patent
Nakayama

(10) Patent No.: US 10,334,143 B2
(45) Date of Patent: Jun. 25, 2019

(54) IMAGE PICKUP APPARATUS HAVING WIRING BOARD WITH ALTERNATELY ARRANGED FLYING LEADS

(71) Applicant: OLYMPUS CORPORATION, Tokyo (JP)

(72) Inventor: Takashi Nakayama, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/786,093

(22) Filed: Oct. 17, 2017

(65) Prior Publication Data

US 2018/0041666 A1 Feb. 8, 2018

Related U.S. Application Data

(63) Continuation of application No. PCT/JP2015/061864, filed on Apr. 17, 2015.

(51) Int. Cl.

| | |
|---|---|
| *H04N 5/225* | (2006.01) |
| *H04N 7/18* | (2006.01) |
| *H01L 27/146* | (2006.01) |
| *H01L 29/423* | (2006.01) |
| *A61B 1/05* | (2006.01) |

(Continued)

(52) U.S. Cl.
CPC ............. *H04N 5/225* (2013.01); *A61B 1/05* (2013.01); *H01L 27/14* (2013.01); *H01L 27/146* (2013.01); *H01L 29/42396* (2013.01); *H04N 5/2251* (2013.01); *H04N 7/183* (2013.01);
(Continued)

(58) Field of Classification Search
CPC .................. H04N 5/225; H04N 7/183; H04N 2005/2255; H04N 5/2251; H01L 27/14; H01L 27/146; H01L 29/42396; H01L 2224/49175; A61B 1/04; A61B 1/05;
(Continued)

(56) References Cited

FOREIGN PATENT DOCUMENTS

| JP | 2013-098182 | * | 5/2013 | ............. H01L 27/14 |
| JP | 2013-098182 A | | 5/2013 | |

(Continued)

OTHER PUBLICATIONS

International Search Report dated Jun. 30, 2015 issued in PCT/JP2015/061864.

*Primary Examiner* — Twyler L Haskins
*Assistant Examiner* — Akshay Trehan
(74) *Attorney, Agent, or Firm* — Scully, Scott, Murphy & Presser, P.C.

(57) ABSTRACT

An image pickup apparatus includes: an image pickup device including a light receiving surface, an opposite surface, and an inclined surface inclined at a first angle, and provided with light receiving surface electrodes on the light receiving surface; a cover glass; and a wiring board including a first main surface and a second main surface, and including wires each connected with each of the light receiving surface electrodes, back surfaces of the light receiving surface electrodes are exposed to a side of the opposite surface, distal end portions of the wires are flying leads bent at a second angle in a relation of a supplementary angle to the first angle and connected with the light receiving surface electrodes, and the second main surface at a distal end portion of the wiring board is directly fixed to the opposite surface arranged in parallel with the second main surface.

3 Claims, 6 Drawing Sheets

(51) Int. Cl.
*H01L 27/14* (2006.01)
*A61B 1/00* (2006.01)

(52) U.S. Cl.
CPC . *A61B 1/00002* (2013.01); *H01L 2224/49175* (2013.01); *H04N 2005/2255* (2013.01)

(58) Field of Classification Search
CPC ....... A61B 1/00; A61B 1/00002; A61B 1/005; A61B 1/042
USPC ................ 348/65, 211.14, 373, 374; 396/17; 600/101
See application file for complete search history.

(56) References Cited

FOREIGN PATENT DOCUMENTS

| | | | | | |
|---|---|---|---|---|---|
| JP | 2014-075764 | * | 4/2014 | ............ | H04N 5/225 |
| JP | 2014-075764 A | | 4/2014 | | |
| JP | 2014-094237 | * | 5/2014 | ............... | A61B 1/04 |
| JP | 2014-094237 A | | 5/2014 | | |
| WO | WO 2014/054419 A1 | | 4/2014 | | |
| WO | WO 2014/065099 A | | 5/2014 | | |

* cited by examiner

IMAGE PICKUP APPARATUS HAVING WIRING BOARD WITH ALTERNATELY ARRANGED FLYING LEADS

CROSS REFERENCE TO RELATED APPLICATION

This application is a continuation application of PCT/JP2015/061864 filed on Apr. 17, 2015, the entire contents of which are incorporated herein by this reference.

BACKGROUND OF THE INVENTION

1. Field of the Invention

The present invention relates to an image pickup apparatus including an image pickup device in which a plurality of electrodes electrically connected with a light receiving portion are lined up, and a wiring board in which a plurality of wires bonded with each of the plurality of electrodes of the image pickup device are lined up.

2. Description of the Related Art

An image pickup apparatus manufactured by a wafer level CSP technique is small-sized so that the image pickup apparatus greatly contributes to diameter reduction of an endoscope.

In a manufacturing method of the image pickup apparatus of a wafer level CSP type, first, on a light receiving surface of a semiconductor wafer, a plurality of light receiving portions and a plurality of light receiving surface electrodes electrically connected with the respective light receiving portions are formed. The light receiving portion is a pixel area formed of a CMOS (complementary metal oxide semiconductor) image sensor, a CCD (charge coupled device), or the like. A glass wafer is joined to the light receiving surface of the semiconductor wafer and a bond wafer is manufactured. Then, a plurality of through wires reaching an opposite surface opposing the light receiving surface of the bond wafer are formed.

The light receiving surface of an image pickup device obtained by cutting the bond wafer is covered with cover glass. However, since the light receiving portions are connected with electrodes on the opposite surface through the through wires, an electric signal can be transmitted and received.

Japanese Patent Application Laid-Open Publication No. 2014-75764 discloses an image pickup apparatus 101 illustrated in FIG. 1. In the image pickup apparatus 101, instead of the plurality of through wires, a plurality of connection wires are arranged in one through trench 110T.

The image pickup apparatus 101 includes an image pickup device 110 to which cover glass 130 is joined by an adhesive layer 120, a wiring board 140, and a signal cable 150. On the image pickup device 110, the through trench 110T with an inclined wall surface is formed. The cover glass 130 and the adhesive layer 120 are extended to an outer side of an end side of the inclined surface, that is, a bottom surface of the through trench 110T. Since light receiving surface electrodes 112 on a light receiving surface 110SA are extended to the bottom surface of the through trench 110T, back surfaces of the light receiving surface electrodes 112 are exposed to the bottom surface of the through trench 110T. On an inclined wall surface (inclined surface) 110SS of the through trench 110T, a plurality of bond electrodes 114 respectively extended from the bottom surface (right above the light receiving surface electrodes 112) of the through trench 110T are lined up. At the bond electrode 114, a bump 115 is disposed. Note that the inclined surface 110SS is inclined at an acute first inclination angle θ1 to the light receiving surface 110SA of the image pickup device 110.

Each of the plurality of bond electrodes 114 is bonded with a plurality of bond electrodes 141 lined up at an end portion of a main surface 140SA of the wiring board 140 through the bump 115. That is, for the wiring board 140, the main surface 140SA is inclined at the first inclination angle θ1 to an opposite surface 110SB of the image pickup device 110. Then, to a second bond electrode (not illustrated) at the other end portion of the wiring board 140, the signal cable 150 is bonded.

Note that the flexible wiring board 140 and the signal cable 150 are arranged within a projection surface of the image pickup device 110, an outer dimension (plane view dimension) of the image pickup apparatus 101 is a same as an outer dimension of the image pickup device 110.

SUMMARY OF THE INVENTION

An image pickup apparatus in an embodiment of the present invention includes: an image pickup device including a light receiving surface where a light receiving portion is formed, an opposite surface opposing the light receiving surface, and an inclined surface inclined at an acute first angle to the light receiving surface, and provided with a plurality of light receiving surface electrodes electrically connected with the light receiving portion and formed on the light receiving surface; a transparent member joined so as to cover the light receiving surface; and a wiring board including a first main surface and a second main surface, and including a plurality of wires each connected with each of the plurality of light receiving surface electrodes of the image pickup device, the transparent member and the plurality of light receiving surface electrodes are extended to an outer side of an end side of the inclined surface, back surfaces of the light receiving surface electrodes are exposed to a side of the opposite surface, respective distal end portions of the plurality of wires are flying leads bent at a second angle in a relation of a supplementary angle to the first angle and electrically connected with each of the light receiving surface electrodes, and the second main surface at a distal end portion of the wiring board is directly fixed to the opposite surface of the image pickup device arranged in parallel with the second main surface.

DETAILED DESCRIPTION OF THE PREFERRED EMBODIMENTS

First Embodiment

Hereinafter, an image pickup apparatus 1 in a first embodiment of the present invention will be described with reference to the drawings. Note that the drawings are schematic, and a relation between a thickness and a width of individual members, a ratio of the thicknesses of the respective members, a number of bond electrodes and an array pit or the like are different from the actual ones. In addition, even between the drawings, a part where the relation of dimensions or the ratio of each other is different is included. Further, for some configurations, for example a silicon oxide layer on a surface of a silicon substrate and wires or the like, illustrations are omitted. In addition, illustrations of electronic components or the like are sometimes omitted.

Figure 1:
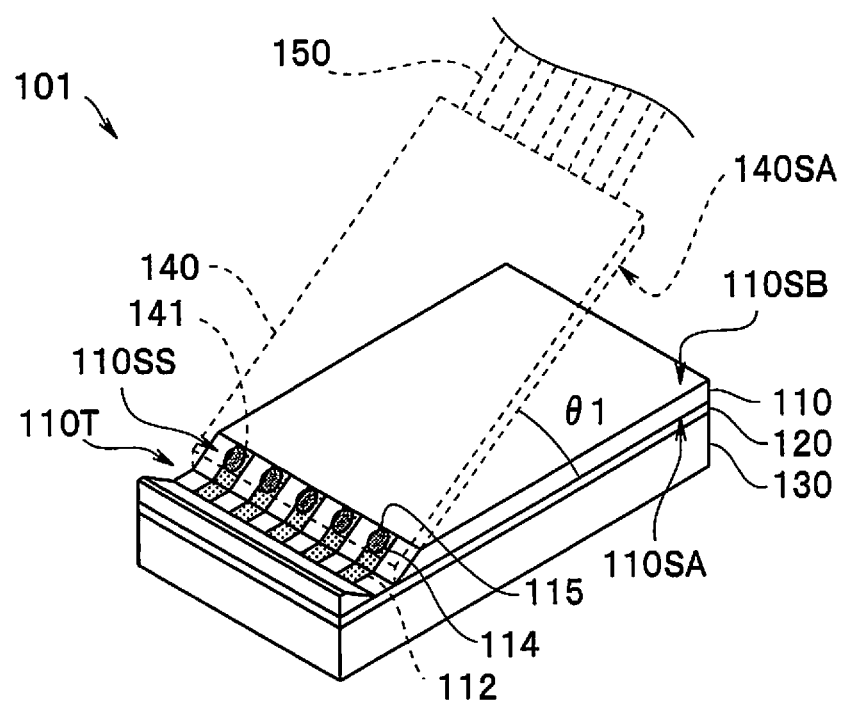
FIG. 1 is a perspective view of a conventional image pickup apparatus.
Figure 2:
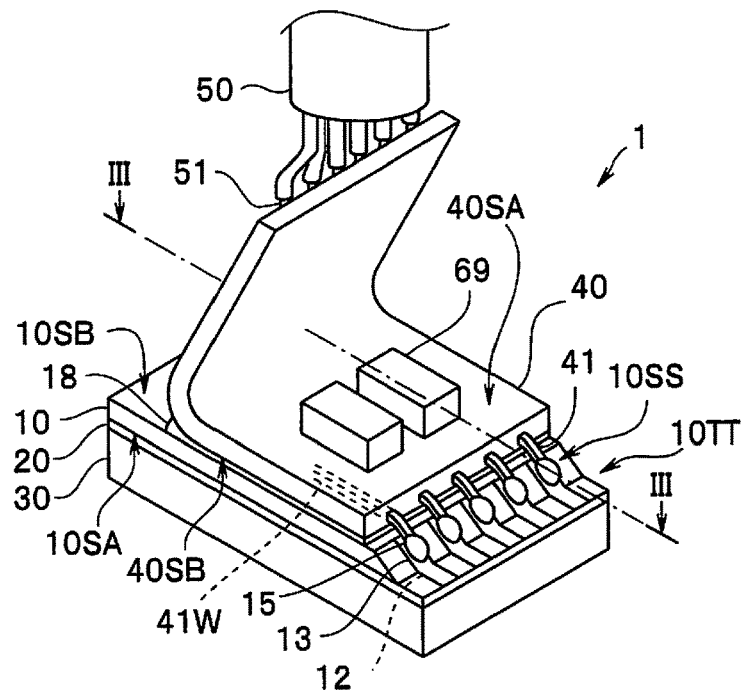
FIG. 2 is a perspective view of an image pickup apparatus in a first embodiment.
Figure 3:
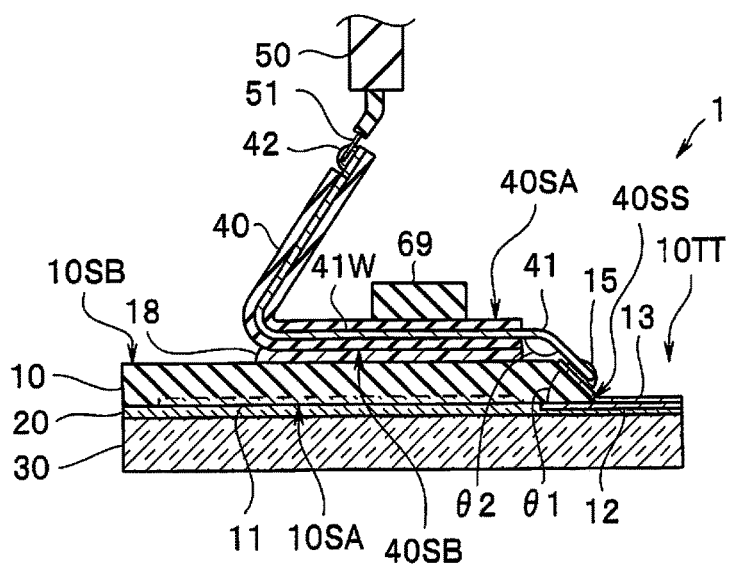
FIG. 3 is a sectional view along a III-III line in FIG. 2 of the image pickup apparatus in the first embodiment.

As illustrated in FIG. 2 and FIG. 3, the image pickup apparatus 1 includes an image pickup device 10 formed of a silicon substrate, cover glass 30 which is a transparent member, a wiring board 40, and a signal cable 50. A light receiving surface 10SA of the image pickup device 10 is covered with the cover glass 30 through an adhesive layer 20.

The image pickup device 10 has a configuration almost same as the configuration of the image pickup device 110 of an already described conventional image pickup apparatus 101. That is, the image pickup device 10 formed of silicon includes the light receiving surface 10SA where a light receiving portion 11 is formed, an opposite surface 10SB opposing the light receiving surface 10SA, and an inclined surface 10SS inclined at an acute first angle $\theta_1$ to the light receiving surface 10SA. On the light receiving surface 10SA, a plurality of light receiving surface electrodes 12 electrically connected with the light receiving portion 11 are formed.

However, differently from the image pickup device 110, in the image pickup device 10, the inclined surface 10SS inclined at the first angle $\theta_1$ to the light receiving surface 10SA is a wall surface not in a through trench (10T) but in a notch 10TT. That is, in a case where a cutting line when cutting a bond wafer is on a bottom surface of the through trench, the through trench is turned to the notch 10TT by cutting.

To form the through trench including the inclined surface 10SS, anisotropic etching can be preferably used. As the anisotropic etching, a wet etching method using a tetramethylammonium hydroxide (TMAH) solution, a potassium hydroxide (KOH) solution or the like is desirable, but a dry etching method such as reactive ion etching (RIE) or chemical dry etching (CDE) is also usable.

For example, in the case of using a silicon substrate of a (100) plane for the light receiving surface 10SA as the image pickup device 10, since an etching speed of a (111) plane is lower than the etching speed of the (100) plane in the anisotropic etching, a wall surface of the through trench becomes the (111) plane, and becomes the inclined surface for which an angle $\theta_1$ with the (100) plane which is the light receiving surface 10SA is 54.74 degrees.

The cover glass 30, the adhesive layer 20 and the light receiving surface electrodes 12 of the image pickup device 10 are extended to an outer side of an end side of the inclined surface 10SS of the notch 10TT (the bottom surface of the through trench 110T). During manufacture, the light receiving surface electrodes 12 are disposed on the light receiving surface of a silicon wafer to be the image pickup device 10, and the cover glass 30 is joined through the adhesive layer 20 onto the light receiving surface electrodes 12. The adhesive layer 20 is formed of a transparent ultraviolet curing type resin for example. Note that a microlens array may be disposed on the light receiving portion 11 and a periphery of the light receiving portion 11 may be joined by the adhesive layer.

The silicon wafer to which a glass wafer to be the cover glass 30 is bonded is etched from the side of the opposite surface 10SB and removed. Therefore, on the bottom surface of the notch 10TT, on the outer side of the end side of the inclined surface 10SS in other words, a back surface of the light receiving surface electrodes 12 is exposed.

Then, on the inclined surface 10SS, bumps 15 of the plurality of inclined surface electrodes 13 electrically connected with the light receiving surface electrodes 12 respectively are lined up. The inclined surface electrodes 13 partially disposed on the back surface of the light receiving surface electrodes 12 are electrically connected with the light receiving portion 11.

The wiring board 40 is a flexible wiring board in which polyimide is an insulating layer for example. Then, a distal end portion of a second main surface 40SB of the wiring board 40 is fixed to the opposite surface 10SB of the image pickup device 10 through an adhesive layer 18 formed of a thermosetting type resin for example.

On a first main surface 40SA, an electronic component 69 such as a chip capacitor is mounted. Note that the electronic component 69 may be mounted also on the second main surface 40SB.

In the wiring board 40, flying leads 41 are lined up on an end face. The flying lead 41 is referred to as an outer lead in a lead frame, and is the distal end portion of a conductor wire 41W for which an insulating base substance of the wiring board 40 is selectively removed. The flying lead 41 can be easily bent. The flying lead 41 is bent at a second angle $\theta_2$ in a relation of the supplementary angle to the first angle $\theta_1$. That is, addition of the first angle $\theta_1$ and the second angle $\theta_2$ is 180 degrees. Therefore, the flying lead 41 is in parallel with the opposite surface 10SB at a proximal end portion and is roughly in parallel with the inclined surface 10SS at a distal end portion. Then, the distal end portion of the flying lead 41 is bonded with the inclined surface electrode 13 of the inclined surface 10SS of the image pickup device 10 through the bump 15. The bump 15 is a solder bump formed of an Sn alloy disposed by a frame plating method or a gold stud bump for example.

Note that the wiring board 40 is a multilayer wiring board including not only a wire 41W of an intermediate layer, the distal end portion of which is the flying lead 41, but also conductor wires (not illustrated) respectively on the first main surface 40SA and the second main surface 40SB, and including insulating layers respectively between the first main surface 40SA and the intermediate layer and between the second main surface 40SB and the intermediate layer. However, even when the wiring board is a single layer wiring board or a both-sided wiring board, as long as the distal end portion of the wire 41W is the flying lead 41, the wiring board can be used as the wiring board 40.

In addition, a bonded part of the flying lead 41 and the inclined surface electrode 13 may be sealed with a sealing resin.

To bond electrodes 42 lined up on a rear end portion side of the second main surface 40SB of the wiring board 40, a conducting wire 51 of the signal cable 50 is bonded. The signal cable 50 is also housed within a projection surface of the image pickup device 10. Note that the plurality of bond electrodes 42 may be disposed on the first main surface 40SA of the wiring board 40, or may be disposed on the first main surface 40SA and the second main surface 40SB.

In the image pickup apparatus 1, for the wiring board 40 and the image pickup device 10, not only the bonded part of the flying lead 41 and the inclined surface electrode 13 but also the second main surface 40SB at the distal end portion of the wiring board 40 and the opposite surface 10SB of the image pickup device 10 arranged in parallel are fixed by the adhesive layer 18. Therefore, the image pickup apparatus 1 has a low risk of being damaged when handled, is easy to manufacture, and is inexpensive because of a high yield.

In addition, the wiring board 40 is bent at the rear end portion not joined with the image pickup device 10. Therefore, in a plane view from a thickness direction of the image pickup device 10, the entire wiring board 40 is arranged in an area on an inner side of the image pickup device 10, that is, within the projection surface of the image pickup device 10. The wiring board 40 may be a non-flexible substrate formed of a glass epoxy resin or the like, however, when a length is long, at least a bending area needs to be flexible in order to house the wiring board 40 within the projection surface of the image pickup device 10.

Since the wiring board 40 and the signal cable 50 are not projected to an outer side of an outer shape of the image pickup device 10, the image pickup apparatus 1 has a narrow diameter.

Note that, when the length of the wiring board 40 is short, it is needless to say that the wiring board 40 can be housed within the projection surface of the image pickup device 10 even when the wiring board 40 is the non-flexible wiring board.

In addition, the distal end portion of the wiring board 40 may be joined with the almost entire opposite surface 10SB of the image pickup device 10, or a bending angle may be an obtuse angle when the wiring board 40 can be housed within the projection surface of the image pickup device 10. Further, for the wiring board 40, not only a bond end portion with the image pickup device 10 is bent but also the rear end portion may be bent further.

Second Embodiment

Next, an image pickup apparatus 1A in a second embodiment will be described. Since the image pickup apparatus 1A is similar to the image pickup apparatus 1 and has same effects, same signs are attached to components of same functions and description is omitted. In addition, in the following figures, the illustrations of the electronic components are omitted.

Figure 4:
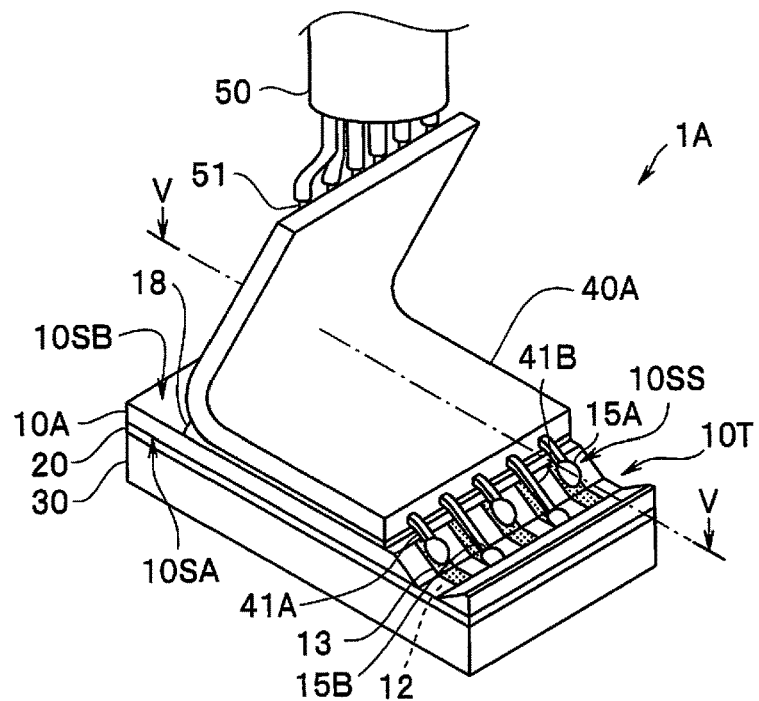
FIG. 4 is a perspective view of an image pickup apparatus in a second embodiment.
Figure 5:
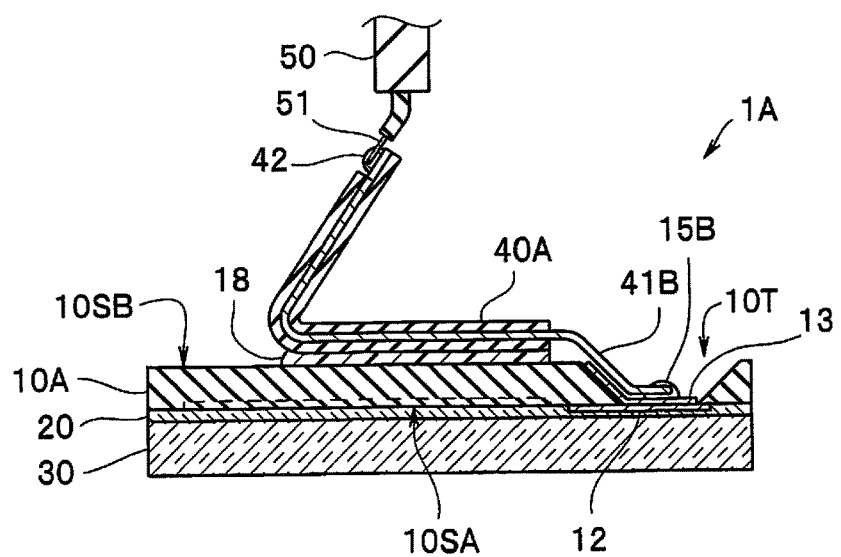
FIG. 5 is a sectional view along a V-V line in FIG. 4 of the image pickup apparatus in the second embodiment.

As illustrated in FIG. 4 and FIG. 5, in the wiring board 40A of the image pickup apparatus 1A, the plurality of flying leads 41 are formed of a plurality of first flying leads 41A and a plurality of second flying leads 41B. The first flying leads 41A and the second flying leads 41B are alternately arranged.

Then, the first flying leads 41A are bonded with the inclined surface electrodes 13 of the inclined surface 10SS through bumps 15A, and the second flying leads 41B are bonded with the light receiving surface electrodes 12 through bumps 15B. The bump 15A and the bump 15B may be the bumps of the same kind, or one may be a solder bump and the other may be a stud bump.

Even when a disposition interval of the plurality of flying leads 41 is narrow, the image pickup apparatus 1A has no risk that the flying leads 41A and 41B adjacent to each other are short-circuited at the bonded part.

Note that, in the image pickup apparatus 1A, similarly to the image pickup device 110 of the conventional image pickup apparatus 101, the inclined surface 10SS inclined at the first angle θ1 is the wall surface in the through trench (10T). Then, in the image pickup apparatus 1A, in the plane view from the thickness direction of the image pickup device 10, the entire wiring board 40A and the signal cable 50 positioned on a rear side of the image pickup device 10A (an opposite side of the cover glass 30) are entirely arranged in the area on the inner side of the image pickup device 10, that is, within the projection surface of the image pickup device 10.

Third Embodiment

Next, an image pickup apparatus 1B in a third embodiment will be described. Since the image pickup apparatus 1B is similar to the image pickup apparatuses 1 and 1A and has the same effects, the same signs are attached to the components of the same functions and the description is omitted.

Figure 6:
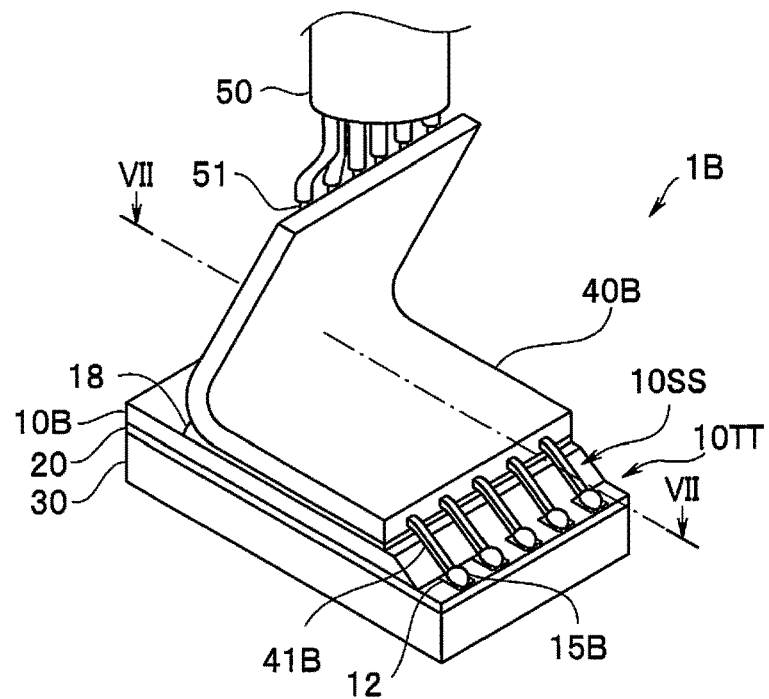
FIG. 6 is a perspective view of an image pickup apparatus in a third embodiment.
Figure 7:
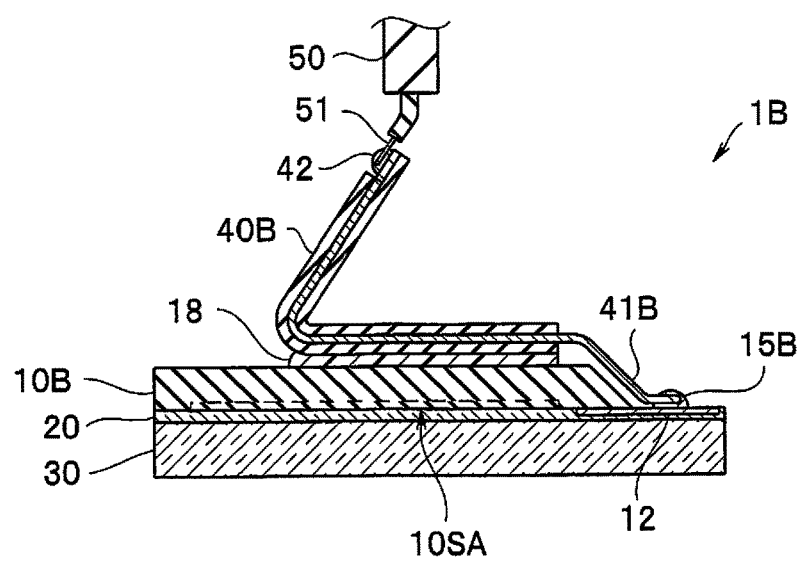
FIG. 7 is a sectional view along a VII-VII line in FIG. 6 of the image pickup apparatus in the third embodiment.

As illustrated in FIG. 6 and FIG. 7, the flying leads 41B of the wiring board 40B of the image pickup apparatus 1B are bonded with the back surface of the light receiving surface electrodes 12 through the bumps 15B.

The bumps 15B on the back surface of the light receiving surface electrodes 12 of the image pickup device 10B are, for example, the solder bumps formed of the Sn alloy disposed by the frame plating method.

Since the inclined surface electrodes are not needed to be disposed, the image pickup apparatus 1B is more easily manufactured than the image pickup apparatus 1.

Fourth Embodiment

Next, an image pickup apparatus 1C in a fourth embodiment will be described. Since the image pickup apparatus 1C is similar to the image pickup apparatuses 1, 1A and 1B and has the same effects, the same signs are attached to the components of the same functions and the description is omitted.

Figure 8:
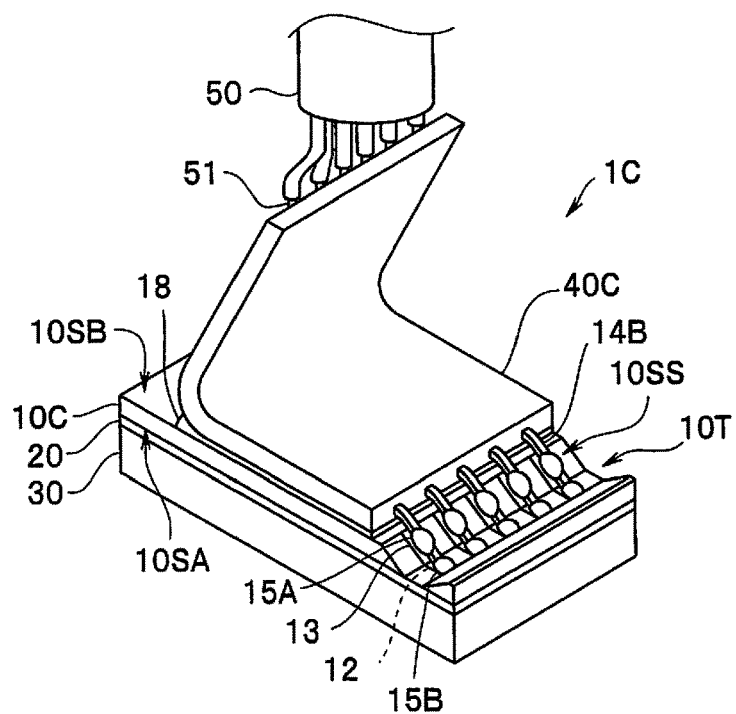
FIG. 8 is a sectional view of an image pickup apparatus in a fourth embodiment.

As illustrated in FIG. 8, the flying leads 41B of the wiring board 40C of the image pickup apparatus 1C are bonded with the inclined surface electrodes 13 of an image pickup device 10C through the bumps 15A, and are bonded with the light receiving surface electrodes 12 through the bumps 15B further.

In the image pickup apparatus 1C, since the flying leads are bonded at two parts, bond reliability is high. Note that the bump 15A and the bump 15B may be the bumps of the same kind, but it is preferable that one is a solder bump and the other is a stud bump. The image pickup apparatus bonded at two parts by different bonding methods has highly bond reliability.

Fifth Embodiment

Next, an image pickup apparatus 1D in a fifth embodiment will be described. Since the image pickup apparatus 1D is similar to the image pickup apparatuses 1 and 1A to 1C and has the same effects, the same signs are attached to the components of the same functions and the description is omitted.

Figure 9:
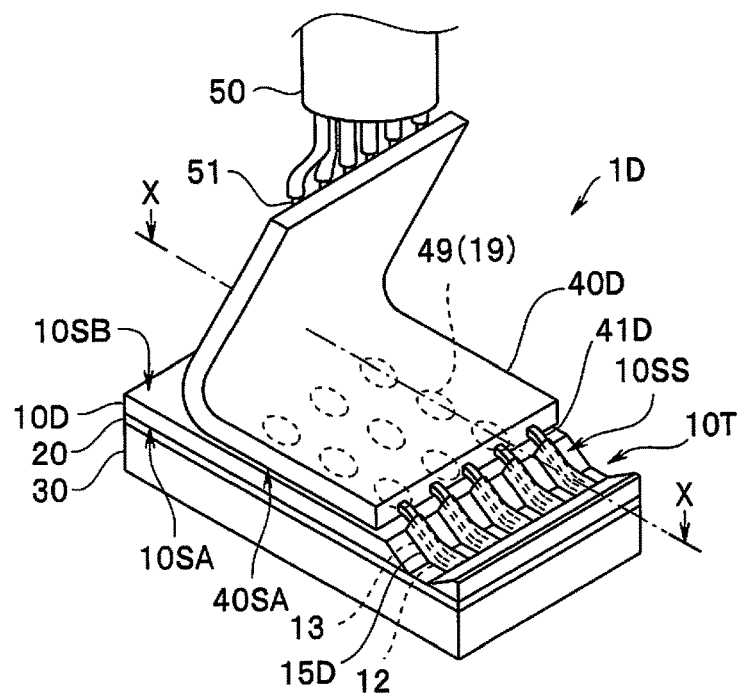
FIG. 9 is a perspective view of an image pickup apparatus in a fifth embodiment.
Figure 10:
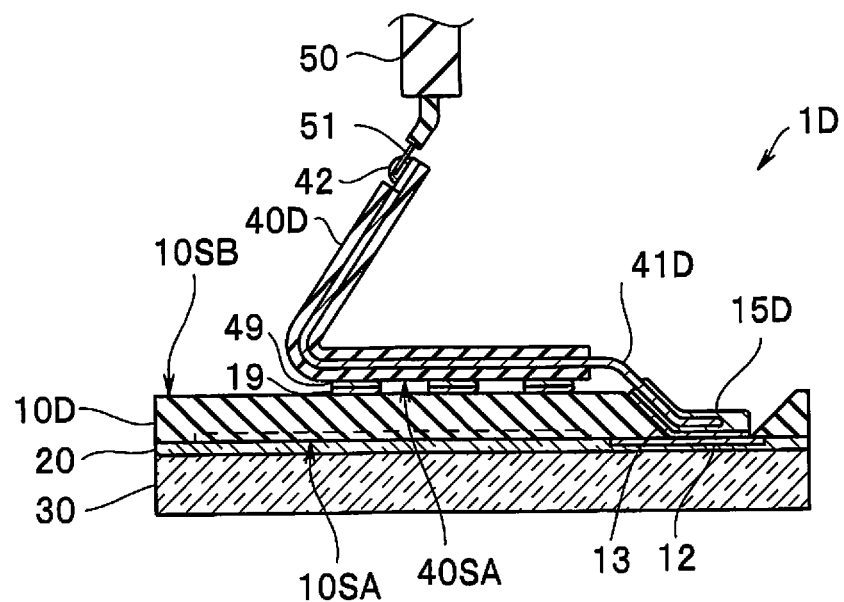
FIG. 10 is a sectional view along an X-X line in FIG. 9 of the image pickup apparatus in the fifth embodiment.

As illustrated in FIG. 9 and FIG. 10, a thick solder layer 15D is formed at the inclined surface electrodes 13 and the light receiving surface electrodes 12 of an image pickup device 10D of the image pickup apparatus 1D. Then, flying leads 41D of a wiring board 40D are bonded with the inclined surface electrodes 13 and the light receiving surface electrodes 12 by and through the solder layer 15D. The solder layer 15D is formed of the Sn alloy disposed by the frame plating method, for example.

In addition, in the image pickup apparatus 1D, a plurality of first bond electrodes 19 are disposed on the opposite surface 10SB of the image pickup device 10D, and a plurality of second bond electrodes 49 are disposed on the distal end portion (distal end face) of the first main surface 40SA of the wiring board 40D. The first bond electrodes 19 are solder-bonded with the second bond electrodes 49.

That is, the plurality of first bond electrodes 19 and the plurality of second bond electrodes 49 are similarly arranged in a matrix. Bumps (not illustrated) are disposed to the first bond electrodes 19. The bumps are formed of the Sn alloy disposed by the frame plating method, for example.

In the image pickup apparatus 1D, since the bond portion of the flying leads 41D and the inclined surface electrodes 13 is long (wide), the bond reliability is high. In addition, since generated heat is transmitted from the opposite surface 10SB through the first bond electrodes 19 and the second bond electrodes 49 to the wiring board 40D, the image pickup device 10D does not easily become a high temperature. Therefore, operations of the image pickup apparatus 1D is stable.

The present invention is not limited to the embodiments and the like described above, and can be variously changed, modified, combined or the like without changing a subject matter of the present invention.

What is claimed is:

1. An image pickup apparatus comprising:
an image pickup device comprising:
   a light receiving surface where a light receiving portion is formed,
   an opposite surface opposing the light receiving surface, and
   an inclined surface inclined at an acute first angle to the light receiving surface, the light receiving surface being provided with a plurality of light receiving surface electrodes electrically connected with the light receiving portion the plurality of light receiving surface electrodes being formed on the light receiving surface;
a transparent cover glass joined so as to cover the light receiving surface; and
a wiring board comprising:
   a first main surface,
   a second main surface, and
   a plurality of wires each connected with each of the plurality of light receiving surface electrodes of the image pickup device,
wherein the transparent cover glass and the plurality of light receiving surface electrodes are extended to an outer side of an end side of the inclined surface, the light receiving surface electrodes extending from the light receiving surface to an extended surface of the transparent cover glass,
back surfaces of the light receiving surface electrodes are exposed to a side of the opposite surface,
respective distal end portions of the plurality of wires are flying leads bent at a second angle in a relation of a supplementary angle to the first angle and electrically connected with each of the light receiving surface electrodes,
the second main surface at a distal end portion of the wiring board is directly fixed to the opposite surface of the image pickup device arranged in parallel with the second main surface;
the image pickup device includes a plurality of inclined surface electrodes respectively extended from the plurality of light receiving surface electrodes to the inclined surface,
the plurality of flying leads are formed of alternately arranged first flying leads and second flying leads,
the first flying leads are bonded with the inclined surface electrodes on the inclined surface, and
the second flying leads are bonded with the light receiving surface electrodes on the extended surface of the transparent cover glass.

2. The image pickup apparatus according to claim 1, wherein a plurality of first bond electrodes are disposed on the opposite surface of the image pickup device, a plurality of second bond electrodes are disposed on a distal end portion of the first main surface of the wiring board, and each of the plurality of first bond electrodes is solder-bonded with each of the plurality of second bond electrodes.

3. The image pickup apparatus according to claim 1, wherein the second main surface at the distal end portion of the wiring board is directly fixed to the opposite surface of the image pickup device to the distal end of the second main surface.

* * * * *

UNITED STATES PATENT AND TRADEMARK OFFICE
CERTIFICATE OF CORRECTION

PATENT NO. : 10,334,143 B2  
APPLICATION NO. : 15/786093  
DATED : June 25, 2019  
INVENTOR(S) : Takashi Nakayama Page 1 of 1

It is certified that error appears in the above-identified patent and that said Letters Patent is hereby corrected as shown below:

In the Claims

Column 7, Claim 1, Line 49 should read:  
light receiving portion, the plurality of light receiving Signed and Sealed this  
Eighth Day of October, 2019

Andrei Iancu  
*Director of the United States Patent and Trademark Office*